United States Patent [19]

Kalopissis et al.

[11] 4,018,556

[45] Apr. 19, 1977

[54] HAIR DYE COMPOUNDS

[75] Inventors: Grégoire Kalopissis, Paris; Andrée Bugaut, Boulogne-sur-Seine, both of France

[73] Assignee: Societe Anonyme dite: L'Oreal, Paris, France

[22] Filed: Aug. 11, 1975

[21] Appl. No.: 603,583

Related U.S. Application Data

[60] Continuation-in-part of Ser. No. 550,583, Feb. 18, 1975, which is a division of Ser. No. 70,480, Sept. 8, 1970, Pat. No. 3,904,690, which is a continuation-in-part of Ser. No. 598,179, Dec. 1, 1966, Pat. No. 3,560,136.

[30] Foreign Application Priority Data

Dec. 3, 1965 Luxembourg .......................... 49990
Apr. 13, 1966 Luxembourg .......................... 50894
Oct. 19, 1966 Luxembourg .......................... 52201

[52] U.S. Cl. ..................................... 8/10.1; 8/10; 260/247.5 R; 260/293.79
[51] Int. Cl.² ...................................... C07D 295/06
[58] Field of Search .............. 260/247.5 R, 293.79; 8/10, 10.1

[56] References Cited

UNITED STATES PATENTS 3,336,308  8/1967  Keck ........................... 260/247.5 R

FOREIGN PATENTS OR APPLICATIONS 1,137,929  6/1957  France ......................... 260/570.5 P
1,408,167  7/1965  France ......................... 260/570.5 P
1,008,844  11/1965  United Kingdom ......... 260/570.5 P

OTHER PUBLICATIONS

King et al., "J. Chem. Soc.," (1948), pp. 1926–1931.

*Primary Examiner*—Henry R. Jiles
*Assistant Examiner*—Robert T. Bond
*Attorney, Agent, or Firm*—Brisebois & Kruger

[57] ABSTRACT

Substituted nitrophenylene-diamine hair dye compounds.

9 Claims, No Drawings

HAIR DYE COMPOUNDS

SUMMARY OF THE INVENTION

This application is a continuation-in-part of application Ser. No. 550,583, filed Feb. 18, 1975, which is a division of application Ser. No. 70,480, filed Sept. 8, 1970, now U.S. Pat. No. 3,904,690, which was a continuation-in-part of application Ser. No. 598,179, filed Dec. 1, 1966, now U.S. Pat. No. 3,560,136.

Products formed from nitrophenylene-diamine by substitution are well known active ingredients used in solutions for coloring keratinic fibers, and particularly human hair.

In order to broaden the range of shades which may be obtained, dyes derived from nitropara-phenylene-diamine or nitro-ortho-phenylene diamine by attaching to at least one of the amine groups connected to the aromatic nucleus, a group, such as an alkyl chain, comprising an extra nuclear amine function have been used. Dyes have also been used in which the amine groups connected to the aromatic nucleus have alkyl or hydroxyalkyl radicals.

The series of derivatives produced from nitropara-phenylene-diamine makes it possible to obtain colors ranging from red to blue; the series produced from nitro-ortho-phenylene diamine makes it possible to obtain orange shades.

Since in practice natural hair shades are obtained by mixing dyes ranging from yellow to blue, it is most important to have hair dyes producing a yellow or yellow-green shade available.

It is an object of this invention to provide yellow dyes having a good affinity for keratinic fibers.

Specifically, it is an object of this invention to provide a new article of manufacture which consists of a water soluble compound which may be used as a dye and has the following formula:

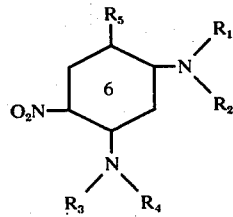

(I)

in which $R_1$, $R_2$, $R_3$, $R_4$ represent an atom of hydrogen, a lower alkyl radical having 1–4 carbon atoms, and at least one of $R_1$, $R_2$, $R_3$ or $R_4$ is a group having the formula:

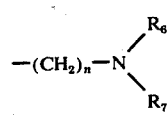

in which $R_6$ and $R_7$ together with the N-atom form a heterocyclic ring, such as morpholino and piperdino, $n$ represents a whole number between 2 and 6 inclusive, and $R_5$ representing a hydrogen atom, lower alkyl radical having 1–4 carbon atoms, a halogen atom or a lower alkoxy radical having 1–4 carbon atoms.

The invention also relates to those quaternary derivatives of the compounds of formula (I) by quaternization of the extra-nuclear amine group at the end of the chain, when said group is a tertiary amine group.

The present invention is also directed to a process for preparing one category of chemical compositions covered by general formula (I) and represented by general formula (II):

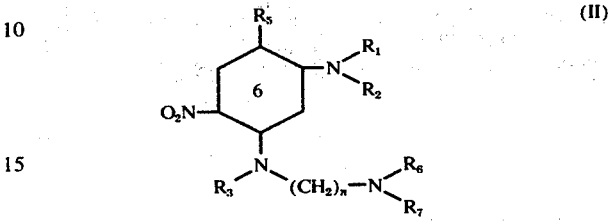

(II)

in which $R_1$, $R_2$, $R_3$, $R_4$, $R_5$, $R_6$, $R_7$ and $n$ have the significances hereinbefore assigned thereto, and especially characterized by the fact that the compound having the formula (III):

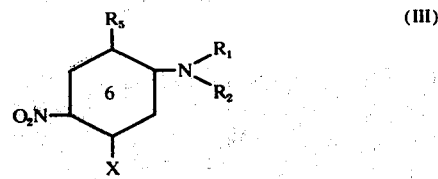

(III)

in which $R_1$, $R_2$ and $R_5$ have the significances hereinbefore assigned thereto and X represents a halogen atom or an $NO_2$ group, is reacted with an aliphatic corresponding to the formula (IV):

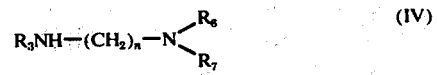

(IV)

in which $R_3$, $R_6$, $R_7$ and $n$ have the significances hereinbefore assigned thereto, said reaction taking place preferably in the presence of a solvent such as pyridine.

A further object of the present invention is to provide a new process for preparing one category of the chemical compositions covered by the general formula (I) and corresponding to the formula (V):

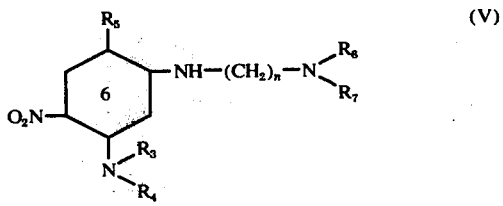

(V)

in which $R_3$, $R_4$, $R_5$, $R_6$, $R_7$ and $n$ have the significances hereinbefore indicated provided $R_3$ and $R_4$ do not represent hydrogen, said process being essentially characterized by the fact that a composition corresponding to formula (VI):

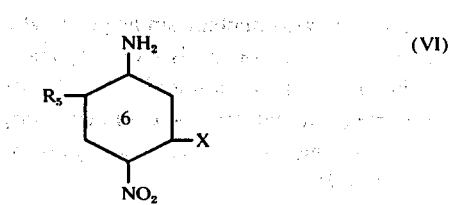

in which $R_5$ has the significance hereinbefore indicated and X represents a halogen atom, is reacted with a secondary amine having the formula (VII):

in which $R_3$ and $R_4$ have the significances hereinbefore indicated; the primary aromatic amine is then converted into a monosubstituted arylsulfonamide by means of an aryl sulfochloride; and that a tertiary aliphatic halogenated amine having the formula (VIII):

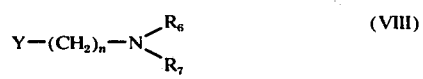

in which Y represents a halogen atom and $R_6$, $R_7$, and n have the significances hereinbefore indicated, is condensed on an alkaline or alkaline-earth derivative of said sulfonamide, after which the product obtained is subjected to acid hydrolysis, and then quaternized.

It should be noted that quaternization of a composition corresponding to formula (I) and having an extra-nuclear tertiary amine group is affected in the conventional way, utilizing a quaternizing agent such as an alkyl or aryl halide or methyl sulfate, in the presence of a solvent.

Preferred quaternizing agents include methyl chloride, methyl iodide, ethyl bromide, phenylchloride benzyl chloride, etc. which produce water soluble quaternary ammonium salts.

Yet another object of the present invention is to provide a hair coloring composition essentially characterized by the fact that it contains at least one dye responding to formula (I) or at least one of the corresponding quaternary compounds.

The coloring compositions according to the present invention make it possible to produce an intense yellow, slightly greenish shade on hair treated therewith. It should be noted that dyes corresponding to formula (I) have a strong affinity for the keratinic fibers of human hair and that the hair coloring compositions which are based on these dyes are particularly resistant to shampooing, but do not color the scalp. Moreover, the shades do not change with the passage of time.

The said hair coloring compositions are simple aqueous solutions of the aforementioned dyes. No oxidizing agents need be added to develop the color when these coloring compositions are used. Various conventional ingredients commonly used in hair dyeing compositions, such as organic solvents, thickening agents, detergents, perfumes, and lacquers, may be added to the hair coloring compositions in question.

The time during which these coloring compositions are left in contact with the hair may be varied within broad limits, but is preferably between 5 and 30 minutes. The temperature at which these compositions are applied may also be varied, but in most cases, they are preferably used at room temperature. The concentration of the dye in the hair coloring solutions may be substantially varied, but this concentration is preferably between 0.01% and 3%.

The coloring compositions according to the invention have, in general, a pH value between 4 and 10, and preferably between 7 and 9. Their pH may be adjusted by using as an alkali either plain ammonia, or any organic base such, for example, as an alkyl amine, an alkanol amine, or a heterocyclic amine.

It should be noted that the new dyes according to the invention may be mixed with each other and may also be mixed with other dyes, whether nitro dyes, azo dyes, anthraquinone dyes, or any of the other types of dye conventionally used for dyeing hair.

It should also be noted that dyes according to formula (I) may also be used for other than cosmetic purposes. In fact, the presence of a primary, secondary or tertiary extra-nuclear aliphatic amine group in the molecule of formula (I) imparts thereto a very substantial potential reactivity which can be put to good use in various synthesizing processes without being adversely affected by the reactivities of the nuclear amines, which are greatly reduced by the presence of a nitro group, whether ortho or para.

The invention also relates to a method of applying hair coloring solutions to the hair, which method comprises the steps of impregnating the hair with a coloring solution which is left in contact with the hair for 5 to 30 minutes, and then rinsing and drying the hair.

Described below by way of non-limiting illustration of the invention are several examples of how to prepare and use these dyes.

EXAMPLE I

Preparation of 1-methyl-2-amino-N-(γ-morpholino propyl)-4-amino-5-nitro-benzene:

The formula for the reaction is:

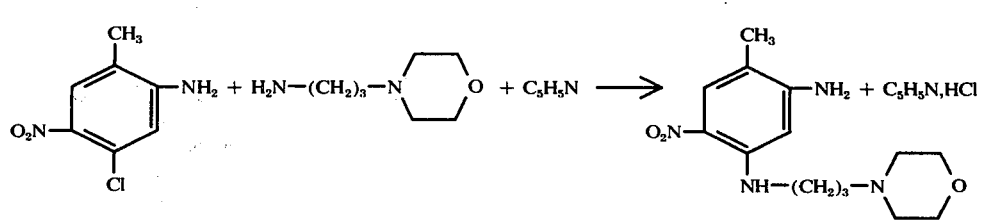

1. The method of preparation:

To 18.65 g (0.1 mole) of 1-methyl-2-amino-4-chloro-5-nitro-benzene dissolved in 40 cc of pyridine, add drop by drop γ-aminopropyl morpholine and heat it to reflux (130°-135° C) for 10 hours. By distillation remove the pyridine in excess and introduce drop by drop the resulting oil obtained into 300 cc of 1N hydrochloric acid. This forms a chestnut colored precipitate which is washed twice with 80 cc of ice water. 23.5 g of a dry product are recovered which is recrystallized in a mixture of alcohol water. After drying, the product melts at 85° C.

2. Analysis:

By adding 5.4% water it is found that the product crystallizes with 0.8 mole of water.

The elementary analysis for $C_{14} H_{22} N_4 O_3 O, 8 H_2O$ gave the following results:

|  | Theory | Found |
|---|---|---|
| % C | 54.19 | 54.42 |
| % H | 7.61 | 7.73 |
| % N | 18.07 | 18.13 |

EXAMPLE II

Preparation of the quaternarium iodide salt of γ[N-(2-nitro-4-methyl-5 amino phenyl)] amino propyl methyl morpholinium:

We quaternized methyl iodide and the compound produced in Example I in the following manner:

To 5.88 g (0.02 mole) of 1-methyl-2-amino- N-(γ-

morpholino propyl) 4-amino-5-nitro-benzene dissolved in 180 cc of toluene, add drop by drop at ambient temperature 8 cc of methyl iodide. Heat the solution in a water bath for 1 hour, let it cool and dry the precipitate obtained. This precipitate is twice washed in hot alcohol. We recovered 5.5 g of product and recrystallized it in a mixture of methanol and water. After drying the product melted at 242° C.

The elementary analysis of the product gave the

|  | Theory | Found |
|---|---|---|
| % C | 41.28 | 41.14 |
| % H | 5.73 | 5.92 |
| % N | 12.84 | 12.72 |

The corresponding piperidino compounds and its quaternary salt can be made in a similar manner except in Example I one would substitute γ-aminopropyl piperidine for the γ-aminopropyl morpholine and the piperidine compound produced can be quaternized with methyl iodide in a manner similar to that described in Example II.

Furthermore both the corresponding morpholino and piperidino compounds can be made using processes similar to those described in the patent application Ser. No. 70,480 in Examples I to XI.

The following examples illustrate dye compositions which contain the compounds of this invention.

EXAMPLE III

The following solution is prepared:

| γ-[N-(2-nitro 4-methyl 5-amino)-phenyl]aminopropyl methyl morpholinium iodide | 0.25 g |
|---|---|
| lauric alcohol condensed with to 10.5 mols of ethylene oxide | 1.5 g |
| $CO_3Na_2$ twice normal q.s.p. | pH = 9 |
| Water, q.s.p. | 100 g |

This dye composition is applied to hair; it is left on the hair for 30 minutes; then the hair is rinsed and washed. The hair has a yellow coloration.

EXAMPLE IV

Preparation of
1-methyl-2-amino-4-N-(β-piperidinoethyl)-amino-5-nitrobenzene:

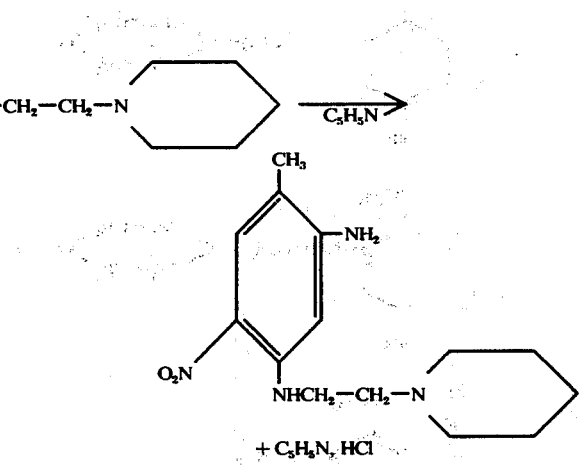

1. The method of preparation:

To 9.37 g (0.05 mole) of 1-methyl-2-amino-4-chloro-5-nitro benzene dissolved in 25 cm³ of pyridine, add rapidly 6.4 g (0.05 mole) of β-aminoethyl piperidine and heat it (110°–115° C) for 8 hours. After cooling a chestnut colored solution is obtained which is added drop by drop under stirring in 170 cm³ of 1N-hydrochloric acid. This forms a orange-yellow colored precipitate which is washed with ice water until neutralization.

11.5 g of a dry product are recovered which is purified by chromatography on a silica column:

5 g of the dry product are dissolved in 300 cm³ of benzene and 10 cm³ of alcohol and the successive used eluates are benzene; benzene-chloroform in a weight proportion of 90:10; benzene-chloroform (50:50); chloroform; and chloroform-absolute alcohol (90:10). The benzene-chloroform (90:10) eluate is recovered. By evaporation an orange precipitate is obtained which after recrystallization in cyclohexane and drying melts at 144° C.

2. Analysis:

The extra nuclear amine is dosed by potentiometry: the found amine number is 3.76 milliequivalent/g (theory 3.60 meq/g)

EXAMPLE V

| Compound of example IV | 0.35 g |
|---|---|
| Butylglycol | 2 g |
| Lauric alcohol condensed with 10.5 mols of ethylene oxide | 2 g |
| Solution of $CO_2Na_2$(twice normal) q.s.p. | pH=9.5 |
| Water, q.s.p. | 100 g. |

This composition is applied to bleached hair for 30 minutes at ambient temperature; the hair rinsed and washed has a yellow coloration.

Other illustrative compounds of this invention include:

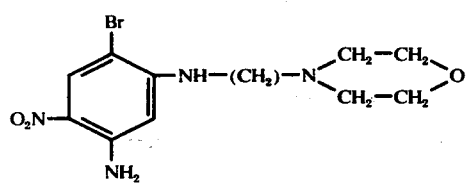

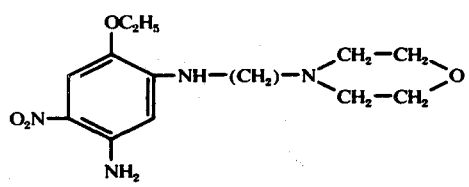

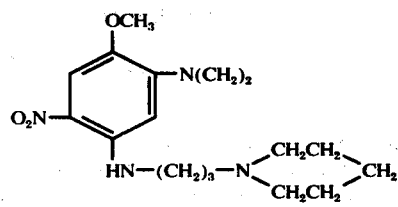

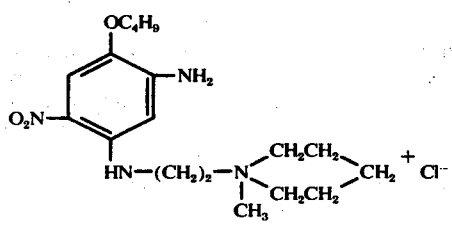

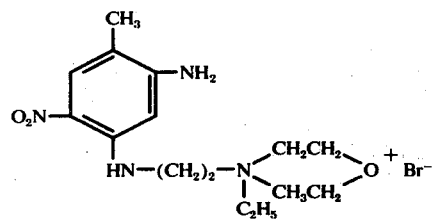

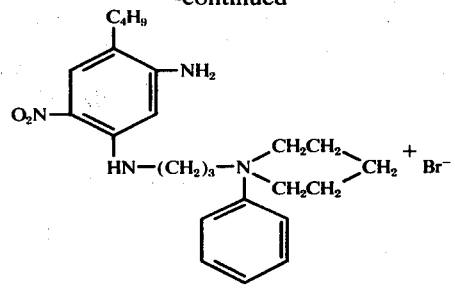

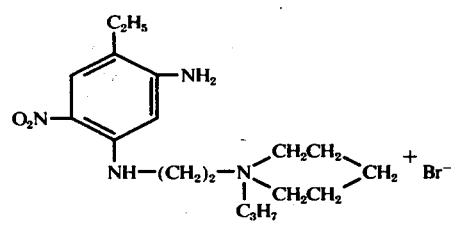

All of the disclosed substitute groups produce dyes that are suitable for dyeing live human hair.

What is claimed is:
1. A water soluble compound having the formula

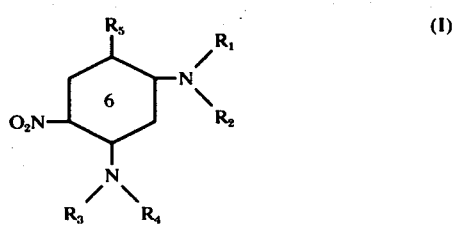

in which $R_1$, $R_2$, $R_3$, $R_4$ are selected from the group consisting of hydrogen, lower alkyl having 1–4 carbon atoms and only one of $R_1$, $R_2$, $R_3$ or $R_4$ is an extra nuclear amino group having the formula:

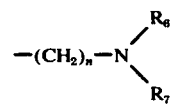

in which $R_6$ and $R_7$ together with the N atom form morpholino and piperdino groups, $n$ represents a number between 2 and 6, and $R_5$ is selected from the group consisting of hydrogen, lower alkyl having 1–4 carbon atoms halogen and lower alkoxy having 1–4 carbon atoms and quaternary ammonium salts of said compound obtained by quaternization of the tertiary extra nuclear amino group.
2. The quaternary ammonium salts of claim 1.
3. The compound of claim 1, in which $NR_6R_7$ is morpholino.
4. The compound of claim 1, in which $NR_6R_7$ is piperdino.
5. The compound of claim 1, in which said compound is a quaternary ammonium salt formed by a quaternizing agent selected from the group consisting of an alkyl or aryl halide.
6. The compound of claim 1, in which said compound is a quaternary ammonium salt formed by the quaternizing agent methyl sulfate.
7. Hair dye compositions which contain a hair coloring amount of the composition of claim 1.
8. Hair dye compositions which contain a hair coloring amount of the composition of claim 2.
9. The process of dyeing live human hair with the composition of claim 7.

* * * * *